United States Patent [19]

Mantegazza et al.

[11] Patent Number: 5,312,987
[45] Date of Patent: May 17, 1994

[54] TWO-STEP PROCESS FOR LIQUID-PHASE PRODUCTION OF OXIMES

[75] Inventors: Maria A. Mantegazza, Monza; Guido Petrini, Galliate; Alberto Cesana, Carate Brianza, all of Italy

[73] Assignee: Enichem Anic S.r.l., Palermo, Italy

[21] Appl. No.: 39,839

[22] Filed: Mar. 30, 1993

[30] Foreign Application Priority Data

Apr. 1, 1992 [IT] Italy .................. MI.92-A/000776

[51] Int. Cl.$^5$ ............................................. C07C 249/04
[52] U.S. Cl. ..................................... 564/267; 564/253; 564/259; 564/265; 564/268
[58] Field of Search ............... 564/253, 259, 265, 267, 564/268, 300, 301; 423/387

[56] References Cited

U.S. PATENT DOCUMENTS

| | | | |
|---|---|---|---|
| 3,655,759 | 4/1972 | Krönig et al. | 260/566 A |
| 4,745,221 | 5/1988 | Roffia et al. | 564/267 |
| 4,794,198 | 12/1988 | Roffia et al. | 564/267 |
| 4,968,842 | 11/1990 | Padovan et al. | 564/253 |
| 5,041,652 | 8/1991 | Padovan et al. | 5674/267 |
| 5,227,525 | 7/1993 | Tonti et al. | 564/259 |

FOREIGN PATENT DOCUMENTS 0208311  7/1986  European Pat. Off. .
0267362  6/1987  European Pat. Off. .
0677386  8/1952  United Kingdom .

OTHER PUBLICATIONS

Windholz et al., *The Merck Index*, 10th Ed. Merck & Co., Inc. Rahway, N.J. USA (1983) p. 4746.
Database WPI Week 9007, Derwent Publications Ltd., London, GB; AN 90-048057 and JP 2,000,754.

*Primary Examiner*—Allen J. Robinson
*Assistant Examiner*—Peter G. O'Sullivan
*Attorney, Agent, or Firm*—George P. Hoare, Jr,

[57] ABSTRACT

Two-step process in the liquid phase for producing oximes at 60°–100° C. and 1.5–5 bars, which comprises:
(a) in a primary step, ammoximating a carbonylic compound with $H_2O_2$ and $NH_3$ in the presence of a silicon, titanium and oxygen based catalyst;
(b) oximating the residual carbonylic compound with a solution of hydroxylamine, obtained in its turn by oxidizing ammonia with $H_2O_2$, having a concentration comprised within the range of from 0.01 to 3%, preferably of from 0.5 to 2% by weight, in such a way as to have a molar ratio of hydroxylamine to the carbonylic compound comprised within the range of from 0.9 to 3, preferably of from 1 to 2.

7 Claims, No Drawings

TWO-STEP PROCESS FOR LIQUID-PHASE PRODUCTION OF OXIMES

The present invention relates to a two-step process for producing oximes in the liquid phase.

More particularly, the present invention relates to a process for producing cyclohexanone oxime.

U.S. Pat. No. 4,794,198 and European patent Nos. 208/311; 267,362; 299/430; 347,926; all to the same Applicant's name, teach that the ammoximation of carbonylic compounds can be effectively carried out in the presence of a silicon, titanium and oxygen based catalyst, which makes it possible very high values of conversion and selectivity to oxime to be achieved. Unfortunately, in practice, above all in the case of cyclohexanone, a complete conversion, which would simplify the operations of oxime separation and recovery, is never reached, with the unreacted carbonylic compound constituting a problem not only due to the need for recovering it, but also owing to the side reactions which it may cause during oxime separation and purification.

The byproducts of these reactions (in the case of cyclohexanone: cyclohexylcyclohexanone, biscyclohexenylcyclohexanone and octahydrophenazine) are known to cause a worsening of the quality of the caprolactam which can be obtained from the subsequent Beckmann rearrangement.

The problem of the incomplete conversion of the carbonylic compound interests both cyclohexanone ammoximation into cyclohexanone oxime, and the ammoximation of other ketones, or aldehydes such, e.g., acetone, methyl ethyl ketone (2-butanone), acetophenone, cyclododecanone, enantic aldehyde (1-heptanal) and so forth.

In order to complete the ammoximation of the residual carbonylic compound, use might be made of the reaction with a hydroxylamine sulfate solution under operating conditions which are well-known in the art. However, hydroxylamine sulfate solutions can only be obtained by means of complex processes such as, e.g., the Raschig process, based on the reduction of nitrogen oxides with ammonium bisulfite.

The present Applicant found now an oximation process which makes it possible the amount of carbonylic compound present in the effluent streams from the primary step of the ammoximation process, to be decreased down to the same levels which can be reached with hydroxylamine sulfate, anyway without using said sulfate—which, as said, can only be produced by means of a considerably complex process.

Therefore, the subject-matter of the present invention is a two-step process for producing oximes in the liquid phase, at 60°–1000° C. and 1.5–5 bars, which process comprises:

(a) in a primary step, ammoximating a carbonylic compound with $H_2O_2$ and $NH_3$ in the presence of a silicon, titanium and oxygen based catalyst;

(b) oximating the residual carbonylic compound with a solution of hydroxylamine, obtained in its turn by oxidizing ammonia with $H_2O_2$, having a concentration comprised within the range of from 0.01 to 3%, preferably of from 0.5 to 2% by weight, in such a way as to have a molar ratio of hydroxylamine to the carbonylic compound comprised within the range of from 0.95 to 3, preferably of from 1 to 2.

The ammoximation reaction of the step (a) is carried out in the presence of suitable solvents. Said solvents, which may be either soluble or insoluble in water, are stable, under the reaction conditions, to the action of hydrogen peroxide and are good solvents for the oximes produced. The ratio of the solvent to the carbonylic compound is generally comprised within the range of from 2.5 to 10 by weight.

Examples of suitable solvents for the process according to the present invention are such tertiary alcohols as t-butyl alcohol, or cyclohexanol or aromatic compounds, such as benzene, toluene, xylenes, chlorobenzene, their mixtures, and so forth.

The ammoximation reaction of the step (a) is preferably carried out in such as way as to reach a conversion of the carbonylic compound, which is higher than 95%, generally comprised within the range of from 96 to 99%. In order to achieve this result, the reaction should preferably be carried out with a molar ratio of $H_2O_2$ to the carbonylic compound comprised within the range of from 0.95 to 1.15, preferably of from 1 to 1.1, and the concentration of ammonia in the liquid reaction media is comprised within the range of from 1 to 2.5%, preferably of from 1.5 to 2% by weight.

The productivity of the primary step is strictly correlated to the concentration of the catalyst suspended in the reaction media.

The concentration of the catalyst should be such as to yield a specific productivity, expressed as parts, by weight, of oxime produced per each part of catalyst per hour, comprised within the range of from 2 to 12, and preferably should be of round 8.

In order to secure an effective dispersion of catalyst throughout the liquid media, the concentration of said catalyst may be comprised within the range of from 1 to 15%, preferably from 1 to 6% by weight. At too low concentrations, the productivity of the primary step becomes too Low and disadvantageous from the ecomonic viewpoint, and at too high concentrations problems of stirring and/or reaction product filtration arise.

As the catalyst, titanium silicalite as disclosed, e.g., in European patent Nos. 267,362 and 299,430, or one of the amorphous compounds disclosed in European patent No. 347,926, may be used.

The catalyst is used in a well-dispersed form in the reaction media, as crystals or microspheres, prepared according to the procedure as disclosed in U.S. Pat. No. 4,701,428.

The size of catalyst particles is generally comprised within the range of from 5 to 100 micrometers.

The operating conditions are, for the primary step, a reaction temperature comprised within the range of from 60° to 1000° C., generally comprised within the range of from 70° to 900° C. At Lower temperatures than this range, the reaction kinetics is rather slow, and at higher temperatures the negative effect of both parallel reactions and consecutive reactions becomes to appear.

The reaction pressure during the primary step should prevent the reaction liquid media from starting boiling and should keep ammonia concentration in the liquid reaction media at the preestablished values. Futhermore, the reaction pressure acts as the drive force for the operation of filtration of the liquid reaction media. Most usual pressure values are comprised within the range of 1.5 to 5 bars, and generally of from 1.8 to 3 bars.

Usually, he residence time is shorter than 120 minutes and generally is comprised within the range of from 30 to 90 minutes.

The exhaustion reaction of the step (b) is a non-catalytic reaction in which the conversion of the carbonylic compound is brought to its completion, in such a way that said carbonylic compound concentration is lower than 200 ppm, preferably lower than 100 ppm, and still more preferably, lower than 50 ppm.

This result can be obtained by bringing the reaction product from the (a) step into contact with a hydroxylamine solution under such conditions as illustrated hereinabove, and keeping the reaction temperature comprised within the range of from 60° to 1000° C., preferably of from 70° to 900° C., and keeping the reaction pressure at a slightly lower value than in step (a). The reaction times are comprised within the range of from 5 to 60 minutes, preferably of from 10 to 40 minutes.

The hydroxylamine solution is obtained by oxidizing ammonia with hydrogen peroxide, in the liquid phase, in the presence of an analogous catalyst to the one used in the primary ammoximation step. Such a catalyst is constituted by silicon, titanium and oxygen, has an either crystalline or amorphous structure and preferably is selected from titanium silicalite and mixed (amorphous) silica-titania oxides.

This type of catalyst is dispersed throughout the reaction media in a finely subdivided form (particle diameter comprised within the range of from 5 to 100 micrometres) in an amount of from 0.1 to 40 parts by weight, preferably of from 1 to 10 parts, per each 100 parts of solution.

The oxidation of ammonia by means of hydrogen peroxide can be accomplished in several ways. One might operate with aqueous ammonia solutions at concentrations comprised within the range of from 1 to 5% by weight, preferably of from 5 to 30%, or with $NH_3$ gas.

Furthermore, the reaction may be carried out either in the absence, or in the presence, of an organic solvent either miscible or immiscible with water, such as $C_1$–$C_6$ aliphatic and cycloaliphatic alcohols (e.g., methanol, ethanol, n- or isobutanol, cyclohexanol, and so on), or $C_5$–$C_8$ aliphatic or aromatic hydrocarbons, such as, e.g., toluene; good results were obtained by using, as the solvent, a tertiary alcohol, in particular t-butanol or t-amyl alcohol. The ratio (by volume) of the solvent to water present is comprised within the range of from 0.5 to 200, preferably of from 4 to 50.

In general, the reaction is carried out with a molar ratio of the reactants to each other ($NH_3:H_2O_2$) comprised within the range of from 0.5 to 200, preferably of from 0.9 to 160. The reaction temperatures are usually comprised within the range of from 25° to 150° C. and preferably of from 40° to 120° C., under the autogenous system pressure, or under higher pressures.

The process of production of hydroxylamine solution can be carried out semicontinuously (with continuous feed of only hydrogen peroxide) or continuously (with both reactants being fed continuously). The effluent stream from the reaction is constituted by a suspension which must be filtered in order to recover the catalyst, which is recycled back to the reaction.

In order to better understand the present invention and to practice it, some illustrative, non-limitative examples are reported.

EXAMPLE 1

Primary step—Ammoximation

To a reactor of 1 liter of capacity equipped with stirring means and continuous feed and discharge systems, the following:

cyclohexanone=70.6 g/h;
t-butanol (12% $H_2O$, by weight)=232.5 g/h;
hydrogen peroxide (at 49.7% by weight)=54.2 g/h (feed molar ratio of $H_2O_2$:ketone=1.1);
ammonia gas: a large enough amount in order to keep ammonia concentration at 2% by weight, relatively to the liquid media.

were fed continuously.

The level of the liquid media was kept at a constant value, by regulating the average residence time at 72 minutes and the concentration of the catalyst was kept constant at approximately 2% by weight (relatively to the liquid media). The catalyst consisted of titanium-silicalite in microspheroidal form (suspended in the liquid media), with a granulometric distribution comprised within the range of from 5 to 100 micrometres, prepared according to Example 1 of U.S. Pat. No. 4,701,428. The reaction temperature was kept constant at 850° C. by means of a thermostatic fluid, circulating inside the reaction jacket. The operating pressure was 2.3 bars.

The resulting product was continuously collected through a porous fitter stick of stainless steel arranged inside the reactor. Pore size: approximately 5 micrometers.

The reactor leaving product (flow rate 380 g/h) had the following composition:

| | |
|---|---|
| cyclohexanone oxime= | 21.0% by weight; |
| cyclohexanone= | 0.3% by weight; |
| water= | 22.0% by weight; |
| ammonia= | 2.0% by weight. | which corresponds to the following results:

| | |
|---|---|
| cyclohexanone conversion: | 98.3% |
| cyclohexanone conversion to oxime: | 99.6% |
| $H_2O_2$ conversion: | 100.0% |
| $H_2O_2$ selectivity: | 89.1% |

Hydroxylamine preparation

To a reactor of AISI 316 steel, of 1.2 liters of capacity, equipped with stirring means and heating jacket, under an inert gas atmosphere the following:

12 g of catalyst consisting of titanium-silicalite in microspheroidal form, prepared according to Example 1 of U.S. Pat. No. 4,701,428;
400 mL of t-butanol;
400 mL of an aqueous solution at 15% by weight of ammonia.

were charged.

To the suspension, kept heated at 8° C., 43.16 g of hydrogen peroxide at 32.44% by weight was added within about 1 minute, with vigorous stirring.

After 1 hour of reaction, the suspension was cooled, discharged and filtered in order to separate the catalyst.

The resulting solution had the following composition:

| | |
|---|---|
| hydroxylamine= | 0.74% by weight; |
| water= | 48.0% by weight; |
| ammonia= | 7.0% by weight; |
| solvent= | balance to 100. |

The yield to hydroxylamine was of 40.7%, based on hydrogen peroxide.

The effluents from the primary ammoximation reactor were fed to a reactor of CSTR (Continuous Stirred Tank Reactor) type, together with those coming from hydroxylamine synthesis.

The amount of hydroxylamine solution fed was such as to keep the molar ratio of NH$_2$OH:cyclohexanone at about 1.7.

The temperature was kept at 85° C.; the operating pressure was of 2 bars.

The average residence time was of 15 minutes, with a cyclohexanone oxime solution being thus obtained, which contained less than 100 ppm of residual cyclohexanone.

EXAMPLE 2

Example 1 was repeated with such an amount of hydroxylamine solution being fed to the exhaustion step as to keep the molar ratio of NH$_2$OH:cyclohexanone at about 1.4.

The average residence time was of 30 minutes, with a cyclohexanone oxime solution being thus obtained, which contained less than 100 ppm of residual cyclohexanone.

EXAMPLE 3

Example 1 was repeated with such an amount of an aqueous solution containing 1.7% of hydroxylamine, by weight, being fed to the exhaustion step as to keep the molar ratio of NH$_2$OH:cyclohexanone at about 1.6.

The hydroxylamine solution was prepared by distilling, under the reduced pressure of 333 mbars, the effluent stream from the ammonia oxidation reactor in such a way as to obtain an overhead stream which consisted of unreacted ammonia and water/t-butanol azeotropic mixture.

With an average residence time of 15 minutes, a cyclohexanone oxime solution was obtained, which contained less than 100 ppm of residual cyclohexanone.

We claim:

1. Two-step process for producing oximes in the liquid phase, at 60°–1000° C. and 1.5–5 bars, which process comprises:
   (a) in a primary step, ammoximating a carbonylic compound with H$_2$O$_2$ and NH$_3$ in the presence of a silicon, titanium and oxygen based catalyst;
   (b) oximating the residual carbonylic compound with a solution of hydroxylamine, obtained in its turn by oxidizing ammonia with H$_2$O$_2$, having a concentration comprised within the range of from 0.01 to 3%, preferably of from 0.5 to 2% by weight, in such a way as to have a molar ratio of hydroxylamine to the carbonylic compound comprised within the range of from 0.95 to 3, preferably of from 1 to 2.

2. Process according to claim 1, in which the ammoximation reaction of the step (a) is carried out in such a way as to reach a carbonylic compound conversion of more than 95%.

3. Process according to claim 2, in which the molar ratio of H$_2$O$_2$ to the carbonylic compound is comprised within the range of from 0.95 to 1.15, and the concentration of ammonia in the liquid reaction media is comprised within the range of from 1 to 2.5%.

4. Process according to any claim 3, in which the catalyst concentration in the primary step is comprised within the range of from 1 to 15% by weight.

5. Process according to claim 4, in which the exhaustion reaction of the step (b) is a non-catalytic reaction in which the conversion of the carbonylic compound is brought to completion in such a way that the its concentration of said carbonylic compound is lower than 200 ppm, preferably lower than 100 ppm.

6. Process according to claim 5, in which the reaction product from the step (a) is brought into contact with a hydroxylamine solution with the reaction temperature being kept comprised within the range of from 60° to 1000° C., and the pressure being slightly lower than in step (a).

7. Process according to claim 5, in which the reaction times are comprised within the range of from 5 to 60 minutes.

* * * * *